(12) United States Patent
Higuchi

(10) Patent No.: US 9,072,459 B2
(45) Date of Patent: Jul. 7, 2015

(54) FUNDUS PHOTOGRAPHING APPARATUS

(71) Applicant: Nidek Co., Ltd., Gamagori-shi, Aichi (JP)

(72) Inventor: Yukihiro Higuchi, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 10 days.

(21) Appl. No.: 13/800,509

(22) Filed: Mar. 13, 2013

(65) Prior Publication Data

US 2013/0242258 A1    Sep. 19, 2013

(30) Foreign Application Priority Data

Mar. 13, 2012 (JP) .................. 2012-056292

(51) Int. Cl.
*A61B 3/14* (2006.01)
*A61B 3/00* (2006.01)
*A61B 3/10* (2006.01)
*G01B 9/02* (2006.01)
*A61B 5/00* (2006.01)

(52) U.S. Cl.
CPC ............ *A61B 3/102* (2013.01); *G01B 9/02064* (2013.01); *G01B 9/0203* (2013.01); *G01B 9/02044* (2013.01); *A61B 5/0066* (2013.01); *G01B 9/02091* (2013.01); *G01B 9/02063* (2013.01); *G01B 9/02068* (2013.01); *G01B 2290/70* (2013.01)

(58) Field of Classification Search
CPC .......... A61B 3/103; A61B 3/14; A61B 3/113; A61B 3/152; A61B 3/1225; A61B 3/1015
USPC .......... 351/205–206, 210, 221, 200, 246, 208
See application file for complete search history.

(56) References Cited

U.S. PATENT DOCUMENTS

2009/0030438 A1    1/2009   Stulen
2009/0303438 A1*  12/2009   Yamada et al. ............... 351/206

(Continued)

FOREIGN PATENT DOCUMENTS

EP    2130486 A1    12/2009
EP    2141446 A1    1/2010

(Continued)

OTHER PUBLICATIONS

Extended European Search Report issued Jun. 25, 2013 corresponds to EP Patent application No. 13159038.2.

*Primary Examiner* — Dawayne A Pinkney
(74) *Attorney, Agent, or Firm* — Rankin, Hill & Clark LLP

(57) ABSTRACT

A fundus photographing apparatus is provided with: a detector that detects an interference state between light reflected from the fundus and reference light; an optical scanner that scans the fundus of an examinee's eye with the measurement light; a focus detection unit that detects a focus position with respect to the fundus of the examinee's eye based on an output signal from a light receiving element that receives the light reflected from the fundus; a focus adjustment unit that corrects the diopter scale with respect to the examinee fundus by moving a first optical member to the focus position; a second optical member disposed in the optical path of the measurement light or the reference light; and an optical path length adjustment unit that adjusts an optical path length difference between the measurement light and the reference light.

10 Claims, 7 Drawing Sheets

(56) References Cited

U.S. PATENT DOCUMENTS

| | | |
|---|---|---|
| 2010/0014089 A1 | 1/2010 | Yamada et al. |
| 2011/0069279 A1 | 3/2011 | Hacker et al. |
| 2011/0176111 A1* | 7/2011 | Taki et al. ............ 351/207 |
| 2012/0249769 A1* | 10/2012 | Naba et al. ............ 348/78 |
| 2013/0188129 A1* | 7/2013 | Inoue ............ 351/206 |

FOREIGN PATENT DOCUMENTS

| | | |
|---|---|---|
| JP | 2009-291252 A | 12/2009 |
| JP | 2009291253 A | 12/2009 |

\* cited by examiner

SCANNING LINE

CHANGE IN LUMINANCE DISTRIBUTION

FUNDUS PHOTOGRAPHING APPARATUS

CROSS-REFERENCE TO RELATED APPLICATION

This application is based on Japanese Patent Application No. 2012-056292 filed with the Japan Patent Office on Mar. 13, 2012, the entire content of which is hereby incorporated by reference.

BACKGROUND

1. Technical Field

The present disclosure relates to a fundus photographing apparatus for capturing a tomographic image of the fundus of an examinee's eye.

2. Related Art

As an optical tomographic image photographing apparatus for capturing a tomographic image of the fundus of an examinee's eye, optical coherence tomography (OCT) which uses low-coherence light is known (see JP 2009-291252 A).

In such an apparatus, an examiner adjusts the focus of the fundus tomographic image by utilizing the focused state of a fundus front image acquired by an SLO optical system or a fundus camera optical system. After the focus adjustment, the examiner optimizes measurement by conducting an optical path length adjustment and a polarization state adjustment (polarizer adjustment).

SUMMARY

A fundus photographing apparatus for obtaining a tomographic image of a fundus of an examinee's eye includes: an interference optical system configured to split a light flux output from a light source into measurement light and reference light, and configured to detect an interference state of the measurement light reflected by the fundus of the examinee's eye and the reference light by a detector; an optical scanner disposed in an optical path of the measurement light to scan the fundus of the examinee's eye with the measurement light; a focus detection unit having a light receiving element for receiving light including reflected light from the fundus of the examinee's eye, and configured to detect a focus position with respect to the fundus of the examinee's eye based on an output signal from the light receiving element; a first optical member disposed in the optical path of the measurement light; a focus adjustment unit that corrects a diopter scale with respect to the examinee fundus by moving the first optical member to the focus position detected by the focus detection unit; a second optical member disposed in the optical path of the measurement light or the reference light; and an optical path length adjustment unit that adjusts an optical path length difference between the measurement light and the reference light, in which the optical path length adjustment unit moves the second optical member to a position at which a tomographic image of the examinee's eye is acquired based on an output signal from the detector during the detection of the focus position by the focus detection unit, and readjusts the position of the second optical member based on the output signal from the detector after the first optical member is moved to the focus position by the focus adjustment unit.

DETAILED DESCRIPTION

Figure 1:
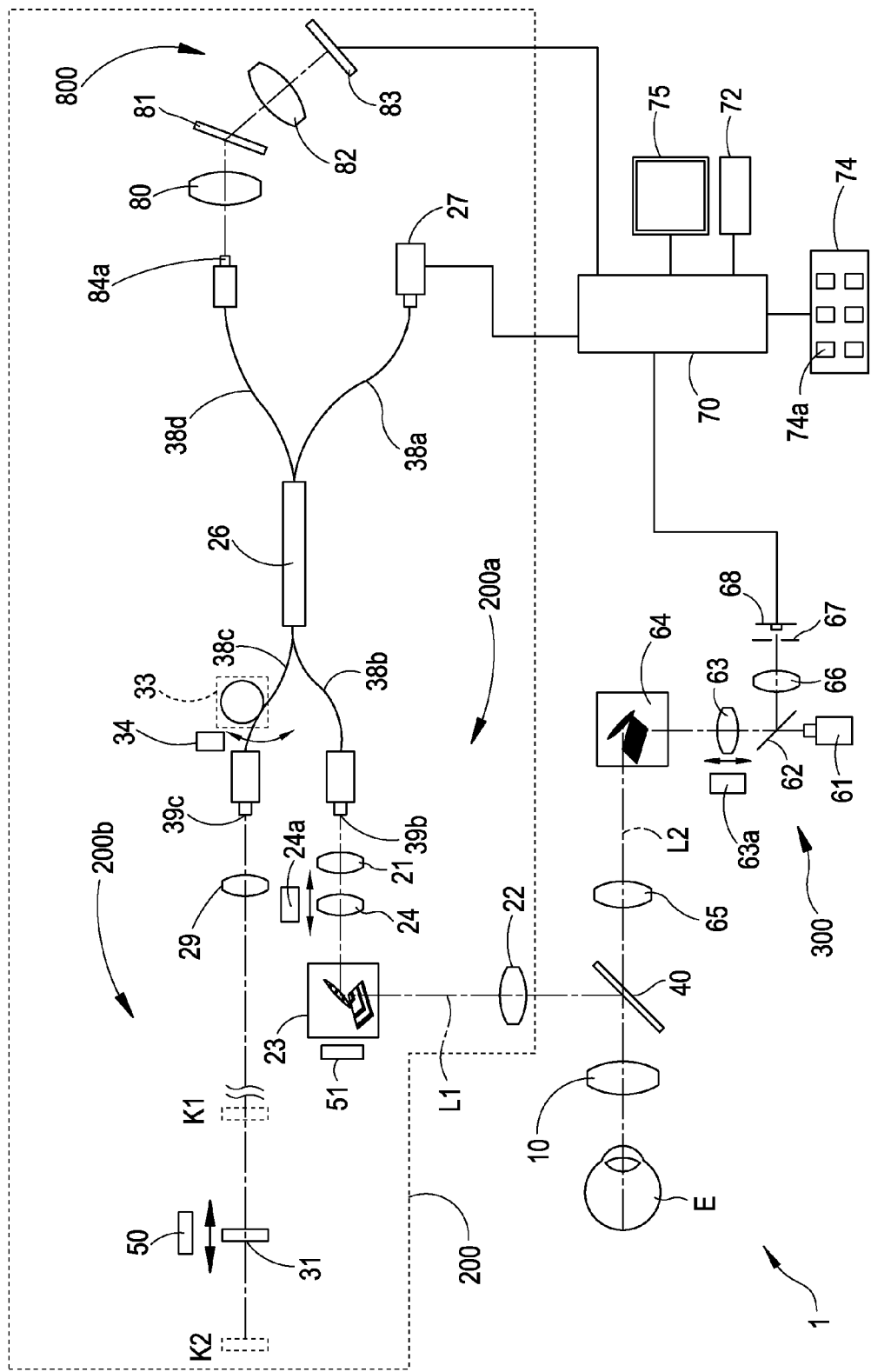
FIG. 1 is a diagram illustrating an optical system and a control system of an ophthalmologic photographing apparatus ("the present apparatus") according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to an optimization technique, an examiner has to stand by for a relatively long period of time until the completion of focus adjustment in order to perform optical path length adjustment. Thus, the examiner may feel stressed, and the stand-by period also puts a burden on an examinee.

An object of the present disclosure is to provide a fundus photographing apparatus that acquires a fundus tomographic image while photographing conditions can be adjusted in a preferred manner.

A fundus photographing apparatus for obtaining a tomographic image of a fundus of an examinee's eye includes: an interference optical system configured to split a light flux output from a light source into measurement light and reference light, and configured to detect an interference state of the measurement light reflected by the fundus of the examinee's eye and the reference light by a detector; an optical scanner disposed in an optical path of the measurement light to scan the fundus of the examinee's eye with the measurement light; a focus detection unit having a light receiving element for receiving light including reflected light from the fundus of the examinee's eye, and configured to detect a focus position with respect to the fundus of the examinee's eye based on an output signal from the light receiving element; a first optical member disposed in the optical path of the measurement light; a focus adjustment unit that corrects a diopter scale with respect to the examinee fundus by moving the first optical member to the focus position detected by the focus detection unit; a second optical member disposed in the optical path of the measurement light or the reference light; and an optical path length adjustment unit that adjusts an optical path length difference between the measurement light and the reference light, in which the optical path length adjustment unit is configured to move the second optical member to a position at which a tomographic image of the examinee's eye is acquired based on an output signal from the detector during the detection of the focus position by the focus detection unit, and readjusts the position of the second optical member based on the output signal from the detector after the first optical member is moved to the focus position by the focus adjustment unit.

According to this apparatus, the fundus tomographic image can be acquired in a state where the photographing conditions are adjusted in a preferred manner.

Hereinafter, an embodiment of the present disclosure will be described with reference to the drawings. FIGS. 1 to 12 are diagrams illustrating a configuration of a fundus photographing apparatus according to the present embodiment. In the present embodiment, the axial direction, horizontal direction, and vertical direction of an examinee's eye (eye E) are referred to as a Z direction, an X direction, and a Y direction, respectively. Thus, the surface direction of the fundus corresponds to the XY direction.

<Outline>

An outline of the fundus photographing apparatus according to the present embodiment will be described. The fundus photographing apparatus (optical coherence tomography device) 1 according to the present embodiment includes an interference optical system (OCT optical system) 200, an observation optical system 300, and a control unit (CPU) 70.

The OCT optical system 200 includes an optical scanner (scanning unit) 23 and a detector 83. A light flux emitted from a light source 27 is split into measurement light and reference light. The measurement light flux is guided to the fundus of the examinee's eye. The reference light is guided to a reference optical system 200*b*. The detector 83 detects the state of interference between the measurement light reflected by the fundus of the examinee's eye (light reflected from the fundus) and the reference light. The control unit 70 obtains a fundus tomographic image of the examinee's eye based on an output signal from the detector 83. The scanning unit 23 is disposed in the optical path of the measurement light. The scanning unit 23 scans the examinee's eye with the measurement light.

For example, the detector 83 of the OCT optical system 200 detects spectral information about the synthetic light of the light reflected from the fundus and the reference light as the state of interference between the measurement light and the reference light. The OCT optical system 200 (or the control unit 70) obtains the fundus tomographic image of the examinee's eye through Fourier analysis of the spectral information.

The observation optical system 300 includes an irradiation optical system for irradiating the fundus of the examinee's eye with illuminating light, and a light receiving optical system. The light receiving optical system includes a light receiving element 68 for receiving the light reflected from the fundus. The observation optical system 300 (or the control unit 70) obtains a front fundus image of the examinee's eye based on an output signal from the light receiving element 68. The light receiving element 68 may be an SLO (scanning laser ophthalmoscope) or a fundus camera, for example.

For example, the observation optical system 300 may be a scanning laser ophthalmoscope (SLO) optical system. The SLO optical system includes an irradiation optical system for irradiating the fundus of the examinee's eye with illuminating light, and a light receiving optical system for receiving the light reflected from the fundus with the light receiving element 68. The SLO optical system further includes a third drive unit (such as a driving mechanism 63*a*). The third drive unit (third drive means) drives a third optical member (such as a focusing lens 63) disposed in the light receiving optical system. The observation optical system 300 (or control unit 70) obtains the front fundus image of the fundus of the examinee's eye based on the output signal from the light receiving element 68.

The fundus photographing apparatus 1 includes a focus detection means (focus detection unit), a focus adjustment means (focus adjustment unit), and an optical path length adjustment means (optical path length adjustment unit).

The focus detection unit includes a light receiving element for receiving light including the light reflected from the fundus. The focus detection unit (or control unit 70) detects a focus position with respect to the fundus of the examinee's eye based on an output signal from the light receiving element.

The focus detection unit may double as the observation optical system 300, for example. In this case, the operation of the focus detection unit is controlled by the control unit 70. In this case, the control unit 70 causes the focusing lens 63 to be moved by controlling the driving mechanism 63*a*. The control unit 70 detects the focus position with respect to the fundus of the examinee's eye based on the front fundus image in accordance with the position of the focusing lens 63.

The focus adjustment unit includes a first drive unit (such as a driving mechanism 24*a*). The first drive unit (first drive means) drives a first optical member (such as a focusing lens 24). The first optical member is disposed in the optical path of the measurement light so as to correct the diopter scale with respect to the examinee's fundus. For example, the focus adjustment unit is controlled by the control unit 70. In this case, the control unit 70 causes the focusing lens 24 to be moved to the focus position detected by the focus detection unit.

The optical path length adjustment unit includes a second drive unit (such as a driving mechanism 50). The second drive unit (second drive means) drives a second optical member (such as a reference mirror 31 disposed in the optical path of the reference light). The second optical member is disposed in the optical path of the measurement light or the reference light so as to adjust an optical path length difference between the measurement light and the reference light. The optical path length difference between the optical path length of the measurement light and the optical path length of the reference light may be changed by a member that changes the optical path length of the measurement light by moving the second optical member disposed in the optical path of the measurement light. Such a member (configuration) is provided by, for example, fixing the reference mirror 31 and moving a relay lens 22 and a fiber end portion 39*b* integrally in the optical system of FIG. 1. In this configuration, the optical path length of the measurement light with respect to the optical path length of the reference light can be also changed.

For example, the operation of the optical path length adjustment unit is controlled by the control unit 70. In this case, the control unit 70 controls the optical path length adjustment unit in parallel with the operation of the focus detection unit (focus position detection). Namely, the control unit 70, based on the output signal from the detector 83, causes the reference mirror 31 to be moved to the position at which the tomographic image of the examinee's eye is acquired. Then, the control unit 70 causes the focusing lens 24 to be moved to the focus position by controlling the focus adjustment unit. Subsequently, the control unit 70 readjusts the position of the reference mirror 31 based on the output signal from the detector 83.

The control of the movement of the reference mirror 31 that is performed in parallel with the operation of the focus detection unit may include moving, based on the output signal from the detector 83, the reference mirror 31 to the position at which the tomographic image of the examinee's eye is acquired, simultaneously with the start of operation of the focus detection unit (start of the focus position detection by the focus detection unit).

For example, the control unit 70, when moving the reference mirror 31 to the position at which the tomographic image of the examinee's eye is acquired, controls the movement of the reference mirror 31 by controlling the driving mechanism 50 based on the output signal from the detector 83 in accordance with the position of the reference mirror 31.

For example, during the readjustment of the reference mirror 31, the control unit 70 determines whether the fundus tomographic image acquired in a predetermined image region is a real image or a virtual image after the focusing lens 24 is moved to the focus position by the focus adjustment unit. The control unit 70 readjusts the reference mirror 31 in accordance with the result of determination.

For example, when moving the reference mirror 31 to the position at which the tomographic image of the examinee's eye is acquired, the control unit 70 roughly adjusts the optical path length based on the signal intensity of the output signal from the detector 83 so that the fundus tomographic image is included in the tomographic image. Further, during the readjustment of the reference mirror 31, the control unit 70 acquires position information about the fundus tomographic image in the depth direction, for example, based on the output signal from the detector 83. On the basis of the acquired position information, the control unit 70 severely adjusts the optical path length so as to acquire the fundus tomographic image at a predetermined depth position.

The fundus photographing apparatus 1 further includes a polarization adjustment means (polarization adjustment unit). The polarization adjustment unit includes a polarization element (such as a polarizer 33) and a polarization element drive means (such as a driving mechanism 34).

The operation of the polarization adjustment unit is controlled by the control unit 70, for example. In this case, the control unit 70 drives the polarizer 33 disposed in the optical path of the measurement light or the reference light. Accordingly, the control unit 70 substantially aligns the polarization states of the measurement light and the reference light. After readjustment of the position of the reference mirror 31, the control unit 70 drives the polarizer 33 based on the output signal from the detector 83 thereby to adjust the polarization states.

In the present embodiment, the control unit 70 may further determine whether or not the optimization adjustment (including optical path length adjustment, focus adjustment, and/or polarization adjustment) has been successful. In this case, the control unit (adjustment determination unit or adjustment determination means) 70 determines whether or not the optimization adjustment has been successful based on the luminance information of the tomographic image. The control unit (adjustment termination unit or adjustment termination means) 70 may terminate the optimization adjustment based on the result of determination.

The control unit 70 may determine the presence or absence of the fundus tomographic image in the tomographic image after the focusing lens 24 (or reference mirror 31) is moved to the focus position by the focus adjustment unit. In this case, upon determining that the fundus tomographic image is absent, the control unit 70 causes the reference mirror 31 to be moved again by controlling the reference mirror 31. Then, the control unit 70 causes the reference mirror 31 to be moved to the position at which the examinee's eye tomographic image is acquired based on the output signal from the detector 83 in accordance with the position of the reference mirror 31.

<Embodiment>

The present embodiment will be described with reference to the drawings. FIG. 1 illustrates the optical system and the control system of the ophthalmologic photographing apparatus (the present apparatus) according to the present embodiment.

The present apparatus is the optical coherence tomography device (OCT device) 1. As illustrated in FIG. 1, the OCT device 1 includes the interference optical system (OCT optical system) 200, the observation optical system (scanning laser ophthalmoscope (SLO) optical system) 300, and the control unit (CPU) 70.

The OCT optical system 200 includes the measurement optical system 200a and the reference optical system 200b. The OCT optical system 200 also includes a spectral optical system 800. The spectral optical system 800 disperses interference light of the reference light and the measurement light in accordance with frequency (wavelength). The dispersed interference light is received by a light receiving means (one-dimensional light receiving element in the present embodiment).

A dichroic mirror 40 reflects the measurement light (for example, $\lambda$=approximately 840 nm) emitted from the measurement light source 27 of the OCT optical system 200. The dichroic mirror 40 transmits the laser light (with a wavelength different from that of the light emitted from the OCT light source 27; for example $\lambda$=approximately 780 nm) emitted from a SLO light source 61 of the SLO optical system 300. The dichroic mirror 40 makes a measurement light axis L1 of the OCT optical system 200 and a measurement light axis L2 of the SLO optical system 300 coaxial.

First, a configuration of the OCT optical system 200 disposed on the reflected side of the dichroic mirror 40 will be described. The OCT light source 27 emits low-coherence light used as the measurement light and reference light for the OCT optical system 200. The OCT light source 27 is an SLD light source, for example. For example, as the OCT light source 27, a light source with the central wavelength of 840 nm and a bandwidth of 50 nm is used. A fiber coupler (splitter) 26 serves as a light splitter member and a light coupler member. The light emitted from the OCT light source 27 is guided via an optical fiber 38a as a light guiding path and split into the reference light and the measurement light by the fiber coupler 26. The measurement light travels via an optical fiber 38b to the examinee's eye E. The reference light travels via an optical fiber 38c and the polarizer (polarization element) 33 to the reference mirror 31.

Along the optical path for outputting the measurement light toward the examinee's eye E, there are disposed the end portion 39b of the optical fiber 38b that outputs the measurement light, a collimator lens 21, a focusing optical member (focusing lens) 24, the scanning unit (optical scanner) 23, a reflective mirror 25, and the relay lens 22. The scanning unit 23 includes two galvanometer mirrors. The scanning unit 23 is driven by a scanning driving mechanism 51. The scanning unit 23 scans the fundus (object) two-dimensionally (in XY direction) with the measurement light. The scanning unit 23 may include an AOM (acoustico-optic element) or a resonant scanner.

The dichroic mirror 40 and the objective lens 10 serves as a light guiding optical system for guiding the OCT measurement light from the OCT optical system 200 to the fundus of the examinee's eye.

The focusing lens 24 is driven by the driving mechanism 24a. The focusing lens 24 is movable in the optical axial direction and used for correcting the diopter scale with respect to the examinee's fundus.

The measurement light output from the end portion 39b of the optical fiber 38b is collimated by the collimator lens 21. Then, the measurement light passes through the focusing lens 24. As the two galvanometer mirrors of the scanning unit 23 are driven, the reflected direction of the measurement light is changed. The measurement light reflected by the scanning unit 23 is reflected by the reflective mirror 25 and then reflected by the dichroic mirror 40 via the relay lens 22. Subsequently, the measurement light is condensed at the fundus of the examinee's eye via the objective lens 10.

The measurement light reflected by the fundus is reflected by the dichroic mirror 40 via the objective lens 10 to travel to the OCT optical system 200. The measurement light travels through the relay lens 22, the reflective mirror 25, the two galvanometer mirrors of the scanning unit 23, the focusing lens 24, and the collimator lens 21, and then enters the end portion 39b of the optical fiber 38b. The measurement light that has entered the end portion 39b travels through the optical fiber 38b, the fiber coupler 26, and an optical fiber 38d, and then reaches an end portion 84a of the optical fiber 38d.

Meanwhile, along the optical path for outputting the reference light toward the reference mirror 31, there are disposed the optical fiber 38c, an end portion 39c of the optical fiber 38c via which the reference light is outputted, a collimator lens 29, and the reference mirror 31. A part of the optical fiber 38c constitutes the polarizer 33. For example, the polarizer 33 includes a metal housing in which a part of the optical fiber 38c is housed in coil shape. The driving mechanism 34 rotates the polarizer 33, whereby the polarization direction of the reference light is changed.

The polarizer 33 according to the present embodiment aligns the polarization directions of the measurement light and the reference light. For this purpose, the polarizer 33 adjusts the polarization direction of at least one of the measurement light or the reference light. The polarizer 33 is disposed on at least one of the measurement optical path or the reference optical path. The polarizer 33 is not limited to the above configuration. The polarizer 33 may be a member that changes the polarization direction of light by adjusting the rotation angle of a ½ wavelength plate or a ¼ wavelength plate about the optical axis. Alternatively, the polarizer 33 may be a member that changes the polarization direction of light by deforming the fiber under pressure.

The reference mirror driving mechanism (second drive unit) 50 drives the reference mirror 31 (second optical member) disposed in the reference optical path so as to adjust the optical path length of the measurement light or the reference light. According to the present embodiment, the reference mirror 31 is disposed in the reference optical path and movable in the optical axial direction. Thus, the reference mirror 31 can change the optical path length of the reference light.

The reference light outputted via the end portion 39c of the optical fiber 38c is made into a parallel light flux by the collimator lens 29. The parallel light flux is reflected by the reference mirror 31 and then condensed by the collimator lens 29 to enter the end portion 39c of the optical fiber 38c. The reference light that has entered the end portion 39c reaches the fiber coupler 26 via the optical fiber 38c and the polarizer 33.

As described above, the reference light produced from the light output from the light source 27 and the light reflected from the fundus which is acquired when the measurement light is reflected by the fundus of the examinee's eye are combined by the fiber coupler 26 into interference light. The interference light passes through the optical fiber 38d and is outputted via the end portion 84a.

The spectral optical system 800 (spectrometer unit) disperses the interference light into frequency components so as to obtain an interference signal for each frequency. The spectral optical system 800 includes a collimator lens 80, a grating mirror (diffraction grating) 81, a condenser lens 82, and the light receiving element (detector) 83. The light receiving element 83 includes a one-dimensional element (line sensor) with sensitivity to light having wavelengths in the infrared region.

The interference light outputted via the end portion 84a is made into parallel light by the collimator lens 80 and then dispersed by the grating mirror 81 into frequency components. The dispersed interference light is condensed via the condenser lens 82 on a light receiving surface of the detector (light receiving element) 83. Thus, spectral information of an interference pattern is recorded on the light receiving element 83. On the basis of an output signal from the light receiving element 83, the control unit 70 obtains a tomographic image of the eye. Namely, the spectral information (light receiving signal) is inputted from the light receiving element 83 to the control unit 70. The control unit 70 analyzes the spectral information by Fourier transform to determine information in the depth direction of the examinee's eye. The control unit 70 can acquire the tomographic image by scanning the fundus with the measurement light in a predetermined transverse direction by using the scanning unit 23. For example, the control unit 70 can acquire a tomographic image (fundus tomographic image) in an X-Z plane or a Y-Z plane of the fundus of the examinee's eye by scanning the fundus with the measurement light in the X direction or Y direction (According to the present embodiment, the system in which the tomographic image is obtained by one-dimensionally scanning the fundus with the measurement light is referred to as a "B scan"). The acquired fundus tomographic image is stored in a memory 72 connected to the control unit 70. The control unit 70 may also be configured to two-dimensionally scan the fundus in the X and Y directions with the measurement light by driving the scanning unit 23. Thus, the control unit 70 can acquire a two-dimensional moving image with respect to the X and Y directions of the fundus of the examinee's eye or a three-dimensional image of the fundus of the examinee's eye based on the output signal from the light receiving element 83.

The reference mirror 31 can be moved in the optical axial direction by being driven by the driving mechanism 50. The range of movement is set to accommodate the differences in the ocular axial length of the individual examinee's eyes. As illustrated in FIG. 1, the reference mirror 31 can be moved in a range between a movement limit position K1 in the direction in which the optical path length of the reference light is decreased and a movement limit position K2 in the direction in which the optical path length of the reference light is increased.

The initial position (movement start position) of the reference mirror 31 prior to the start of an automatic optical path length adjustment (first automatic optical path length adjustment, the details of which will be described later) is set at the movement limit position K1 or the movement limit position K2. Of course, the initial position may be a position between the position K1 and the position K2 (intermediate position). The initial position may be set to be arbitrarily changeable.

The focusing lens (focusing optical member) 24 is moved in the optical axial direction by being driven by the driving mechanism 24a. The movable range of the focusing lens 24 is between the first movement limit position and the second movement limit position. For example, the first movement limit position is a position corresponding to the refractive power of −12D, namely, the position at which focus is achieved with the refractive power of −12D. For example, the second movement limit position is a position corresponding to the refractive power of +12D.

The initial position of the focusing lens 24 is a position corresponding to the average eye refractive power of the examinee's eye (such as the position corresponding to the refractive power of 0D). Of course, other positions may be set as the initial position. The initial position may be set to be arbitrarily changeable. The initial position may be the first movement limit position or the second movement limit position.

The polarizer 33 is rotated by being driven by the driving mechanism 34. The range of rotation of the polarizer 33 is between a first rotation limit position (such as 0°) and a second rotation limit position (such as 180°).

The angle (rotated position) of the polarizer 33 is provided between the first rotation limit position and the second rotation limit position. The polarizer 33 is not rotated until a second automatic optical path length adjustment (to be described later) is completed. Thus, the initial position of the polarizer 33 is between the limit positions (intermediate position).

Next, the SLO optical system (confocal optical system) 300 disposed in the transmission direction of the dichroic mirror 40 will be described. The SLO optical system 300 is used as the observation optical system for acquiring a front image of the fundus of the examinee's eye. The SLO optical system 300 includes an irradiation optical system for irradiating the fundus of the examinee's eye and a light receiving optical system. The light receiving optical system includes a light receiving element. The light receiving element receives reflected light from the examinee's eye irradiated by the irradiation optical system. The front image of the fundus of the examinee's eye is obtained based on a light receiving signal output from the light receiving element.

The SLO light source 61 is a light source that emits high-coherency light. The SLO light source 61 includes a laser diode light source with λ=780 nm, for example. In the optical path for outputting the laser light from the SLO light source 61 toward the examinee's eye E, the focusing lens 63, a scanning unit 64, a relay lens 65, and the objective lens 10 are disposed. The focusing lens 63 is movable in the optical axial direction in accordance with the refraction error of the examinee's eye. The scanning unit 64 includes a combination of a galvanometer mirror and a polygon mirror. These mirrors are driven by the scanning driving mechanism 52 so as to cause the measurement light to scan the fundus in the XY direction at high speed. The reflective surfaces of the galvanometer mirror and the polygon mirror are disposed at positions substantially conjugated with the pupil of the examinee's eye.

A beam splitter 62 is disposed between the SLO light source 61 and the focusing lens 63. A condenser lens 66, a confocal opening 67, and a SLO light receiving element 68 are disposed in the reflected direction of the beam splitter 62. The condenser lens 66 is included in the confocal optical system. The confocal opening 67 is placed at a position substantially conjugated with the fundus.

The laser light (measurement light) emitted from the SLO light source 61 passes through the beam splitter 62 and then reaches the scanning unit 64 via the focusing lens 63. The direction where the laser light is reflected is changed by the galvanometer mirror and the polygon mirror. The laser light reflected by the scanning unit 64 passes through the relay lens 65 and the dichroic mirror 40. Then, the laser light is condensed via the objective lens 10 at the fundus of the examinee's eye.

The laser light reflected by the fundus passes through the objective lens 10, the relay lens 65, the galvanometer mirror and the polygon mirror of the scanning unit 64, and the focusing lens 63 and is reflected by the beam splitter 62. Subsequently, the laser light is condensed by the condenser lens 66 and then received by the light receiving element 68 via the confocal opening 67. The light receiving element 68 that has received the laser light outputs a light receiving signal to the control unit 70. The control unit 70 acquires a front image of the fundus of the examinee's eye based on the light receiving signal. The acquired front image is stored in the memory 72. An SLO image is acquired through a longitudinal scan (sub-scan) of the laser light by the galvanometer mirror provided in the scanning unit 64 and a lateral scan (main scan) of the laser light by the polygon mirror.

The control unit 70 is connected to the display monitor 75 and controls an image displayed on the display monitor 75. To the control unit 70, the memory 72, an operating unit 74, the reference mirror driving mechanism 50, the driving mechanism 63a, the driving mechanism 24a, the driving mechanism 34 and the like are connected. The driving mechanism 63a moves the focusing lens 63 in the optical axial direction. The driving mechanism 24a moves the focusing lens 24 in the optical axial direction.

Figure 2:
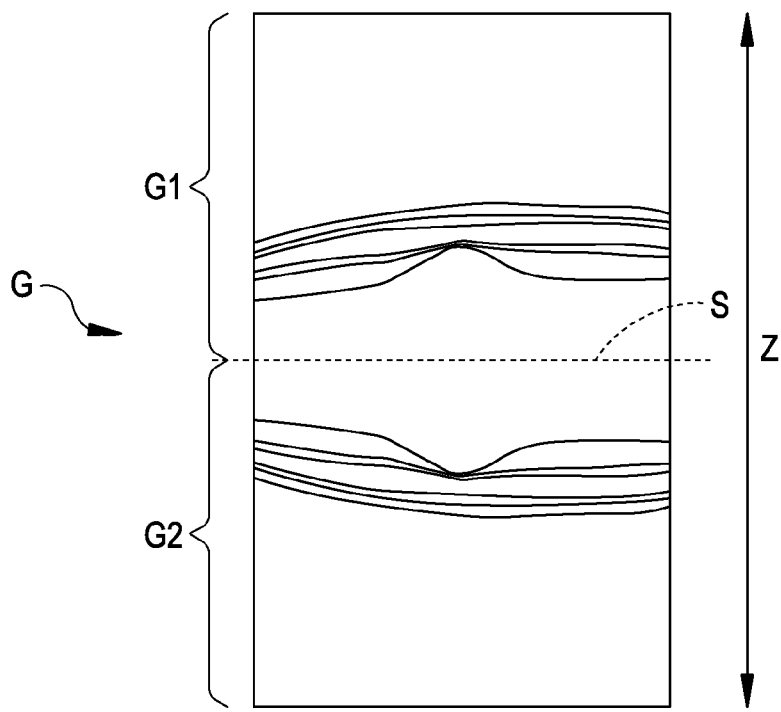
FIG. 2 is a diagram illustrating an example of a tomographic image acquired by an OCT optical system.

FIG. 2 is a diagram illustrating an example of a tomographic image acquired (formed) by the OCT optical system 200. In the present apparatus, a tomographic image in the vicinity of a depth position S of the fundus at which the measurement light and the reference light have the same optical path lengths can be obtained. An image range (photographing range) G that can be obtained in the present apparatus includes a first image range G1 and a second image range G2. The first image range G1 covers data of an image corresponding to a position in the back of the fundus with respect to the depth position S. The second image range G2 covers data of an image corresponding to a position in front of the fundus with respect to the depth position S. The images in the first image range G1 and the second image range G2 are symmetrical with respect to the depth position S.

When the reference mirror 31 is disposed such that the depth position S is provided at the front of the retinal surface, a fundus tomographic image (normal image) with higher sensitivity on the retinal surface side than on the choroid side portion is acquired. In this case, the fundus tomographic image obtained from the first image range G1 and the fundus tomographic image obtained from the second image range G2 faces each other (the portions of the images corresponding to the retina are adjacent to each other). In this case, a real image is acquired from the first image range G1 while a virtual image (mirror image) is acquired from the second image range G2.

On the other hand, when the reference mirror 31 is disposed such that the depth position S is provided at the rear of the retinal surface, a fundus tomographic image (inverse image) with higher sensitivity on the choroid side portion than on the retinal surface side is acquired. In this case, the fundus tomographic image obtained from the first image range G1 and the fundus tomographic image obtained from the second image range G2 face in opposite directions (the portions of the images corresponding to the choroid are adjacent to each other). In this case, a real image is acquired from the second image range G2 while a virtual image (mirror image) is acquired from the first image range G1.

For example, the control unit 70 selects the first image range G1 or the second image range G2 as the image range for acquiring the real image, and displays the selected image range on the screen of the monitor 75. According to the present embodiment, the control unit 70 is set to select the first image range G1.

According to the present embodiment, the control unit 70 subjects spectral information (spectral data) output from the light receiving element 83 to a dispersion correction process by software. The control unit 70 obtains a depth profile based on the spectral information after dispersion correction. Thus, an image quality difference is caused between the real image and the virtual image.

For example, the control unit 70 acquires a first dispersion correction value (for normal image) from the memory 72 as a dispersion correction value for correcting the influence of dispersion on the real image. The control unit 70 corrects the spectral information output from the light receiving element 83 by using the first dispersion correction value. The control unit 70 forms fundus tomographic image data through Fourier transform of the corrected spectral information (spectral intensity data). Thereby, the real image acquired from the first image range G1 is turned into an image with high-sensitivity and high-resolution. On the other hand, the virtual image acquired from the first image range G1 is blurred and has low resolution due to the difference in dispersion correction value.

Of course, the above is merely an example and a dispersion correction may be performed on the virtual image by software. The control unit 70 may be set to acquire a real image from the second image range G2. Further, the control unit 70 may be set to acquire real images from both the first image range G1 and the second image range G2. The image range for acquiring the real image may be arbitrarily selected by the examiner operating a predetermined switch.

<Control Operation>

A control operation of the present apparatus with the above configuration will be described. The control unit 70 acquires an OCT image and an SLO image for each frame by controlling the driving of the OCT optical system 200 and the SLO optical system 300. The control unit 70 updates the OCT image and the SLO image displayed on the monitor 75 as needed by controlling the monitor 75. The position for acquiring the initial OCT image that is not dependent on the examiner setting may be set at a scan position (such as in the X direction) with reference to the central position of the SLO image, for example.

Figure 3:
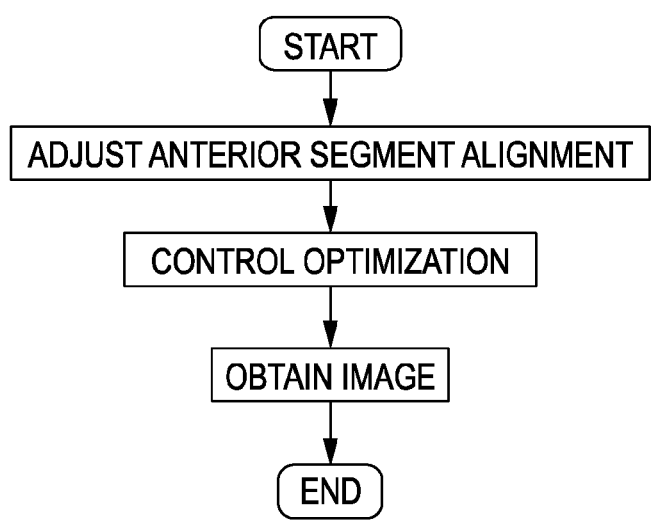
FIG. 3 is a flowchart illustrating the flow of operation in the present apparatus.

FIG. 3 is a flowchart illustrating the flow of operation in the present apparatus. The examiner instructs the examinee to gaze a fixation target on a projection unit, which is not illustrated. Then, the examiner performs an alignment operation by using a joy stick, which is not illustrated, while watching an anterior segment observed image obtained by an anterior segment observation camera, which is not illustrated, on the monitor 75, so as to position the measurement light axis at the pupil center of the examinee's eye. In this way, the alignment for the examinee's eye is completed. Then, the front image of the fundus of the examinee's eye (SLO fundus image) is acquired by the SLO optical system 300. The SLO fundus image is displayed on the monitor 75.

Then, photographing condition optimization (optimization of the OCT optical system 200) is performed, so that the examiner can observe a fundus site of interest to the examiner with the OCT optical system 200 at high sensitivity and high resolution. In the present embodiment, optimization of the OCT optical system 200 is performed through optical path length adjustment, focus adjustment, and polarization state adjustment (polarizer adjustment).

The examiner presses an optimization start switch (optimize switch) 74a disposed on the operating unit (control unit) 74. In response to an operating signal from the optimization start switch 74a, the control unit 70 produces a trigger signal to start optimization.

After completion of optimization, the examiner presses a photography switch which is not illustrated, whereby a fundus tomographic image is obtained and stored in the memory 72.

<Optimization Control>

Figure 4:
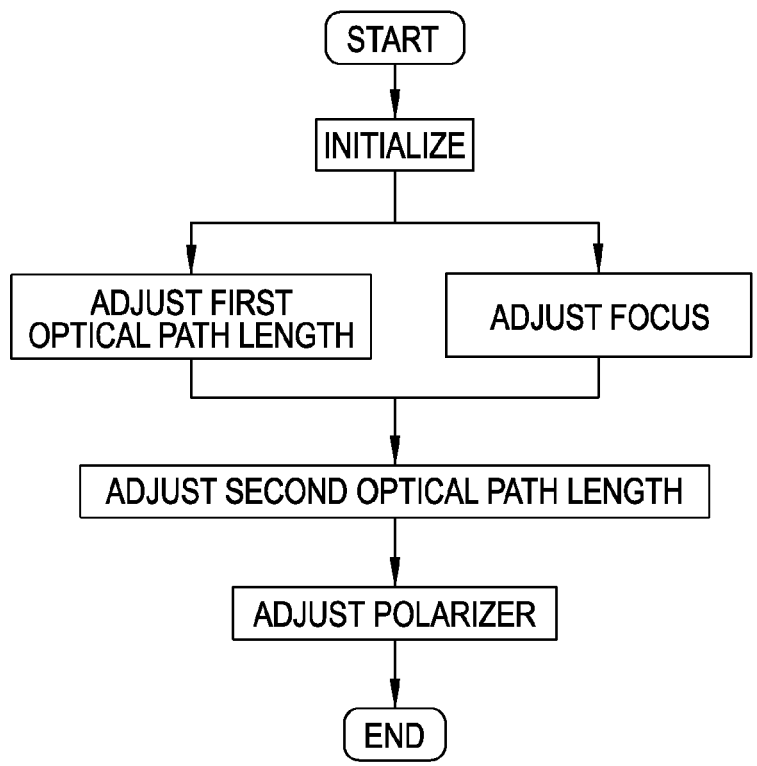
FIG. 4 is a diagram illustrating optimization control according to the present embodiment.

FIG. 4 is a diagram for describing optimization control according to the present embodiment. The control unit 70, when initializing the present apparatus, sets the positions of the reference mirror 31 and the focusing lens 24 at initial positions. The control unit 70 then performs the first optical path length adjustment by causing the reference mirror 31 to be moved from the set initial position in one direction in predetermined steps (first automatic optical path length adjustment). In parallel with the first optical path length adjustment, the control unit 70 also acquires the focus position information with respect to the fundus of the examinee's eye based on the SLO fundus image, which is acquired based on the light receiving signal output from the light receiving element 68. The control unit 70 causes the focusing lens 24 to be moved to the focus position based on the focus position information. Namely, the control unit 70 performs an autofocus adjustment (focus adjustment). It is sufficient if the focus position is provided such that a contrast of a tomographic image that can be permitted as an observed image can be acquired. The focus position may not need to correspond to the position at which an optimum focused state is obtained.

After the focus adjustment is completed, the control unit 70 causes the reference mirror 31 to be moved again in the optical axial direction. Thereby, the control unit 70 performs a second optical path length adjustment, which is an optical path length readjustment (fine adjustment of the optical path length). After the second optical path length adjustment is completed, the control unit 70 drives the polarizer 33 so as to adjust the polarization state of the reference light. Thereby, the control unit 70 adjusts the polarization state of the measurement light.

Hereinafter, an example of optimization control will be described.

<Evaluation Value>

According to the present embodiment, the first automatic optical path length adjustment and the polarizer adjustment are performed by detecting the signal intensity of the tomographic image. In the following description, a predetermined evaluation value B is used as an index for indicating the signal intensity.

Figure 5:
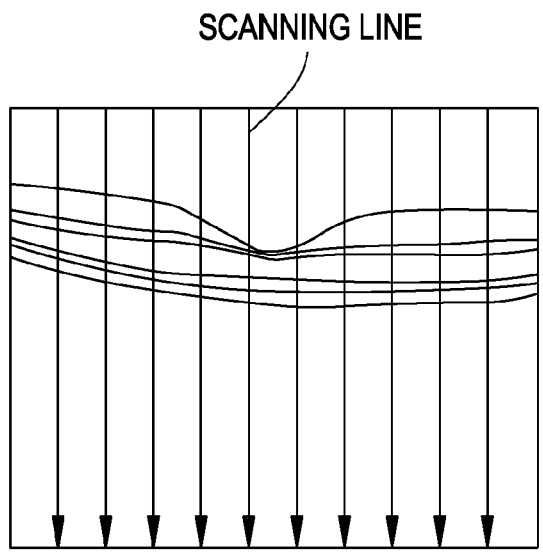
FIG. 5 is a diagram illustrating scanning lines set for acquiring luminance distribution data of a tomographic image.

The evaluation value B is determined by the formula of B=((average maximum luminance value of image)−(average luminance value of background region of image))/(standard deviation of luminance value of background region). The control unit 70 acquires the luminance distribution data of the tomographic image acquired based on the light receiving signal from the light receiving element 83. For example, FIG. 5 is a diagram illustrating an image displayed on the screen of the monitor 75 when the reference mirror, the focusing lens, and the polarizer are disposed at predetermined positions.

Figure 6:
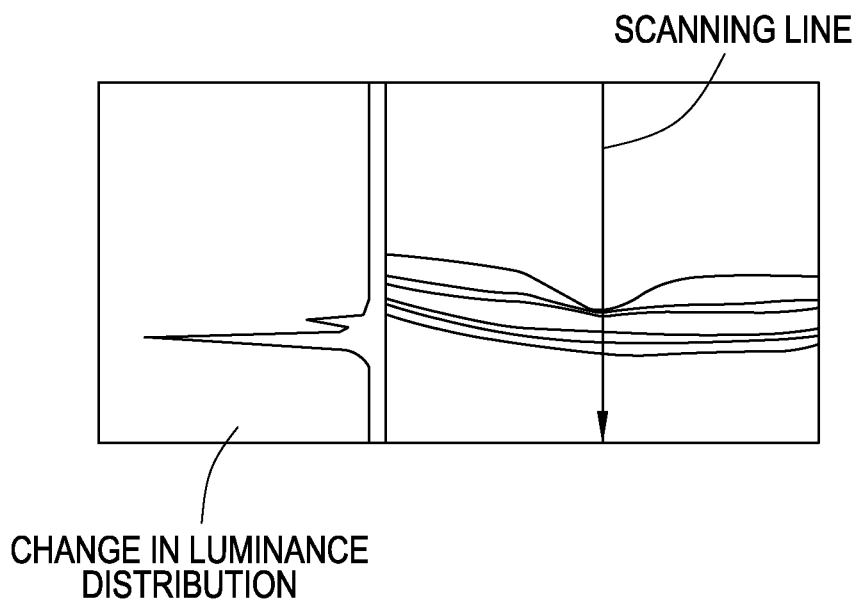
FIG. 6 is a diagram illustrating changes in luminance distribution in an image depth direction.

First, the control unit 70 sets a plurality of scanning lines corresponding to scanning in a depth direction (A scan direction). Further, the control unit 70 obtains the luminance distribution data on each scanning line. In the example illustrated in FIG. 5, the scanning lines are ten division lines dividing the image into ten segments. FIG. 6 is a diagram illustrating a change in luminance distribution in the image depth direction.

The control unit 70 calculates the maximum luminance value from the luminance distribution corresponding to each scanning line. The control unit 70 then calculates an average value of the maximum luminance values for the scanning lines as the maximum luminance value for the fundus tomographic image. Further, the control unit 70 calculates an average value of the luminance values of the background region in the scanning lines as the average luminance value of the background region in the fundus tomographic image.

The evaluation value B thus calculated is utilized for the first automatic optical path length adjustment and the polarizer adjustment. In this case, preferably, the evaluation value B is calculated by using the tomographic image obtained from the first image range G1.

<Initialization>

First, the control unit 70 initializes the present apparatus. During initialization, the control unit 70 causes the reference mirror 31 and the focusing lens 24 to be moved to their initial positions (movement start positions).

During initialization, the control unit 70 selects the movement limit position K1 or the movement limit position K2 as the initial position for the reference mirror 31. Specifically, the control unit 70 selects the movement limit position which is closer to the position of the reference mirror 31 before the start of initialization, as the initial position. The control unit 70 then causes the reference mirror 31 to be moved toward the selected initial position. Of course, the initial position and the direction of movement of the reference mirror 31 may be determined according to a different reference.

The control unit 70 also causes the focusing lens 24 to be moved to its initial position (corresponding to 0D according to the present embodiment).

Then, the control unit 70 starts the first optical path length adjustment and the focus adjustment. Hereinafter, control operations for the respective adjustments will be described.

<Focus Adjustment>

After the initialization control is completed, the control unit 70 produces a trigger signal for starting focus adjustment control. Thus, focus adjustment for the OCT optical system 200 is started. According to the present embodiment, the focus adjustment for the OCT optical system 200 is performed based on the focus position information about the focusing lens 63 of the SLO optical system 300.

First, the control unit 70 starts the focus adjustment for the SLO fundus image. The control unit 70 acquires the focus position information about the SLO optical system 300 based on the SLO fundus image which is acquired based on the light receiving signal output from the light receiving element 68. The control unit 70 causes the focusing lens 63 disposed in the SLO optical system 300 to be moved to the focus position (first focus adjustment).

More specifically, first, the control unit 70 subjects the image data of the SLO fundus image acquired based on the light receiving signal output from the light receiving element 68 to differential processing. On the basis of the result of the differential processing, the control unit 70 acquires differential histogram information. Namely, the control unit 70 filters the image data of the SLO fundus image acquired by the SLO optical system 300 for edge extraction (by Laplacian transform or SOBEL, for example). Thereby, the control unit 70 converts the SLO fundus image into a contour image. Thereafter, the control unit 70 produces a contour image histogram.

Figure 7:
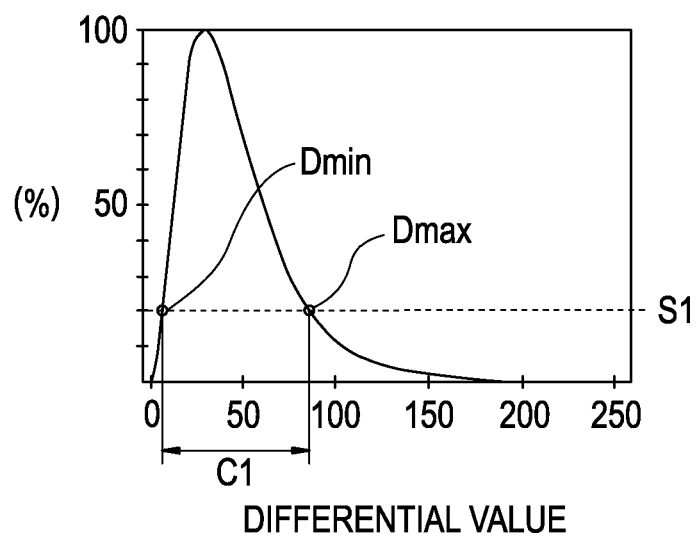
FIG. 7 is a diagram illustrating an example of a differential histogram obtained by differentiating an image signal of an SLO fundus image acquired by an SLO optical system.

FIG. 7 is a diagram illustrating an example of a differential histogram. The differential histogram is obtained by subjecting an image signal of the SLO fundus image acquired by the SLO optical system 300 to differential processing. In FIG. 7, the horizontal axis shows absolute differential values (hereinafter referred to as "differential values") d (d=1, 2, ..., 254). The vertical axis shows the number of pixels H(d) corresponding to the differential values, which is normalized by the number of pixels H (dp) at the differential value indicating a peak number of pixels ((H(d)/H(dp)), in percentage (%). In the histogram of FIG. 7, data for the two points at the end points (d=0, d=255) are excluded. The differential values d are luminance values of the contour image expressed in 255 gradation levels.

In the differential histogram H(d), when the focus is appropriate, the edge of a blood vessel portion of the fundus is sharpened. Thus, the number of pixels for greater differential values is increased. As the focus is displaced, the edge becomes less sharp. Accordingly, when the focus is displaced, the number of pixels for greater differential values is decreased.

On the basis of the differential histogram information acquired as described above, the control unit 70 determines, from the image as a whole, the maximum value of the luminance value (differential value) that has the number of pixels not less than a predetermined ratio. The control unit 70 calculates an image formation state (focused state) evaluation value for the SLO fundus image by using the maximum value. For example, an image formation state evaluation value C1 is a value for evaluating the image formation state of the SLO fundus image. For example, the image formation state evaluation value C1 is the difference between the maximum value Dmax and the minimum value Dmin of the differential values at a threshold value S1 (such as 20%) or more (C1=Dmax−Dmin). The threshold value S1 is set to a value such that the influence of noise can be avoided. Further, the threshold value S1 is set to a value such that the evaluation value C1 can be sensitively changed in response to a change in the image formation state of the SLO fundus image. According to the present embodiment, the threshold value S1 is set on the order of 20% so that the change in edge sharpness in the fundus blood vessel portion, which occupies a small portion of the SLO image as a whole, can be accurately detected. The image formation state evaluation value C1 may be set to the maximum value Dmax of the differential values at the threshold value S1 or more.

The image formation state evaluation value C1 shows a high value when the focusing lens 63 is at the focus position (when the SLO fundus image is in focus). As the focusing lens 63 is displaced from the focus position, the image formation state evaluation value C1 becomes smaller. Thus, the image formation state evaluation value C1 can be used for judging the focused state of the SLO fundus image (image formation state).

The control unit 70 samples the image formation state evaluation value C1 while moving the position of the focusing lens 63 disposed in the light receiving optical system of the SLO optical system 300. On the basis of the result of sampling, the control unit 70 judges the focused state and drives the focusing lens 63 to the focus position.

For example, the control unit 70, in order to search for the proper focus position, controls the driving mechanism 63*a* and causes the focusing lens 63 to be moved to a plurality of moving positions set discretely in the movable range for the focusing lens 63. In this way, the control unit 70 acquires an SLO fundus image corresponding to each moving position. Then, the control unit 70 calculates the image formation state evaluation value C1 corresponding to the moving position by generating the differential histogram for each SLO fundus image. The control unit 70 may continuously move the focusing lens 63. In this case, the control unit 70 may continuously calculate the image formation state evaluation value C1.

Figure 8:
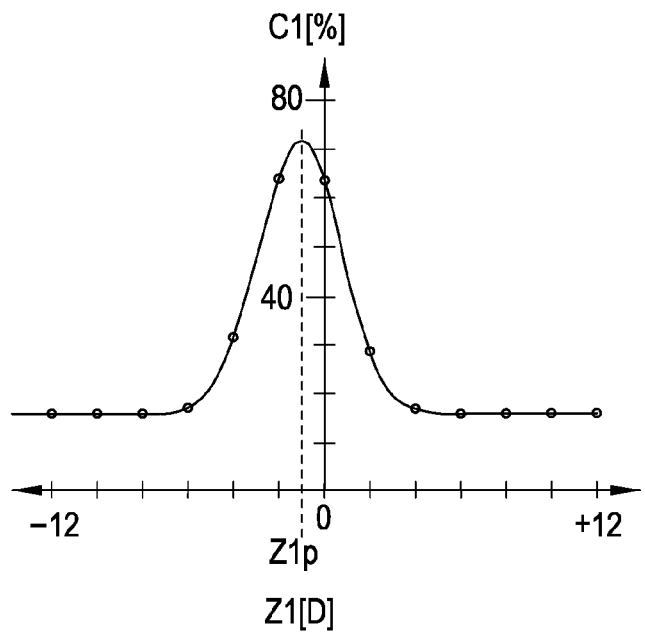
FIG. 8 is a diagram illustrating an example of a graph depicting the relationship between an image formation state evaluation value and the moving position of a focusing lens.

FIG. 8 is a diagram illustrating an example of a graph depicting the relationship between the image formation state evaluation value C1 and a moving position Z1 of the focusing lens 63. When generating the graph of FIG. 8, the control unit 70 causes the focusing lens 63 to be moved in the plus direction from the position corresponding to −12D to the position corresponding to +12D in steps of 2D successively, while the control unit 70 calculates the evaluation value C1 successively.

As described above, the evaluation values C1 for the respective focus positions are discretely obtained. Then, the control unit 70 performs interpolation processing for the characteristics of the evaluation value C1 corresponding to the moving position Z1 of the focusing lens 63. Thereby, the control unit 70 detects the focus position of the SLO optical system 300. For example, the control unit 70 acquires a curve approximating the characteristics of the evaluation value C1 by using a function with the maximal value in the movable range of the focusing lens 63. The control unit 70 acquires a moving position Z1$p$ at which the evaluation value C1 is at the maximum in the curve as the focus position information for the SLO optical system 300. The technique for detecting the focus position of the SLO optical system 300 by interpolation processing described above may include calculation of functional approximation, center of gravity, or an average value.

The control unit 70 causes the focusing lens 63 to be moved to the moving position corresponding to the focus position information acquired as described above by controlling the driving mechanism 63*a*. Thus, the focus adjustment for the SLO fundus image is completed.

Next, the control unit 70 causes the focusing lens 24 of the OCT optical system 200 to be moved based on the focus position information for the SLO optical system 300 that has been obtained by the first focus adjustment (second focus adjustment).

Based on the focus position information about the SLO optical system 300 that has been obtained by the first auto-focus control, the control unit 70 acquires the focus position information about the OCT optical system 200. The control unit 70, based on the focus position information, causes the focusing lens 24 to be moved to the focus position (auto-focus for the OCT image). Here, the control unit 70 acquires the moving position of the focusing lens 63 that has been obtained by the first focus adjustment as the focus position information about the OCT optical system 200. The control unit 70 causes the focusing lens 24 to be moved to the focus position by controlling the driving mechanism 24*a* based on the focus position information.

For example, when the focus position for the SLO optical system 300 corresponds to −3D, the control unit 70 controls the focus position for the OCT optical system 200 to similarly correspond to −3D. In this case, the moving position of the focusing lens 63 and the moving position of the focusing lens 24 may be associated with each other by diopter conversion. In this way, the focus position for the OCT optical system 200 can be easily set to the focus position corresponding to the focus position for the SLO optical system 300.

Thus, the focusing lens 24 of the OCT optical system 200 is moved to the moving position corresponding to the focus position for the SLO optical system 300. As a result, the light reflected from the fundus that enters the fiber end portion 39*b* is increased.

<First Automatic Optical Path Length Adjustment (Coarse Adjustment)>

Figure 9:
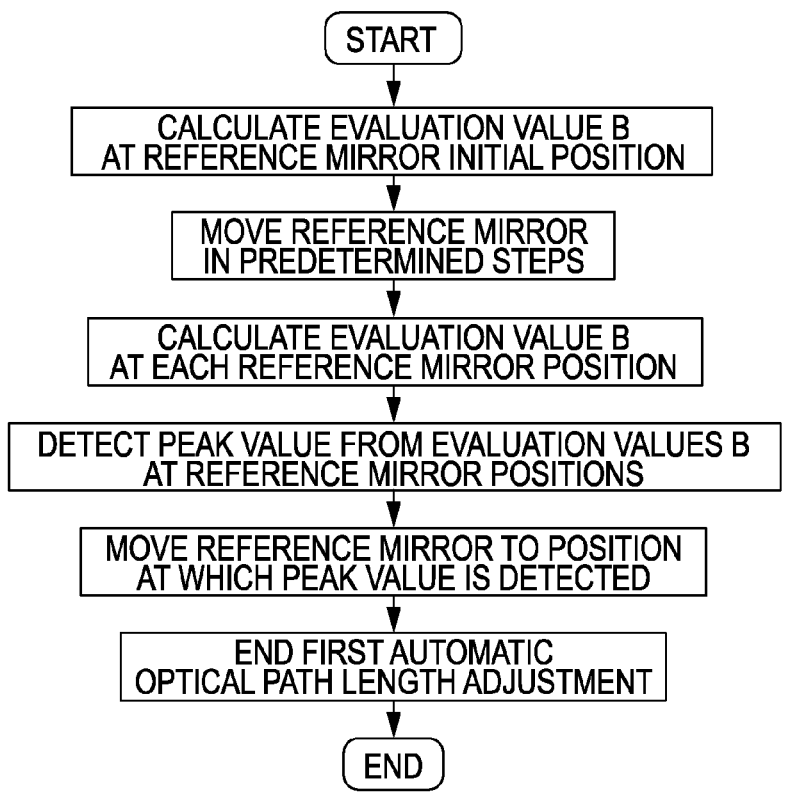
FIG. 9 is a flowchart illustrating the flow of a control operation for a first automatic optical path length adjustment.

As described above, the control unit 70 performs the operation for detecting the focus position and the operation for moving the focusing lens 63 to the detected focus position. In parallel with these operations, the control unit 70 performs a first automatic optical path length adjustment (automatic coarse optical path length adjustment). FIG. 9 is a flowchart illustrating the flow of a control operation for the first automatic optical path length adjustment.

The control unit 70 causes the reference mirror 31 to be moved by controlling the driving mechanism 50. Further, the control unit 70 acquires, based on the output signal from the light receiving element 83 in accordance with the position of the reference mirror 31, a position at which a fundus tomographic image can be acquired, and causes the reference mirror 31 to be moved to such a position.

Specifically, the control unit 70 acquires a tomographic image at the initial position. Then, the control unit 70 causes the reference mirror 31 to be moved toward a movement limit position different from the initial position. For example, when the limit position K1 is selected (set) as the initial position for the reference mirror 31, the control unit 70 causes the reference mirror 31 to be moved toward the limit position K2.

Here, the control unit 70 causes the reference mirror 31 to be moved in predetermined steps (such as in steps of 2 mm as a photographing range), and successively acquires the tomographic images corresponding to the moving positions. In this way, the control unit 70 searches for the position of the reference mirror 31 at which the fundus tomographic image can be acquired.

In this case, the control unit 70 acquires the tomographic image each time the reference mirror 31 is stopped at the discretely set moving positions. Then, the control unit 70 analyzes the tomographic image corresponding to the position. For example, the control unit 70 calculates the evaluation value B for the tomographic image corresponding to each position. The control unit 70 then stores the evaluation value B for the tomographic image in the memory 72 in association with the position of the reference mirror 31.

Figure 10:
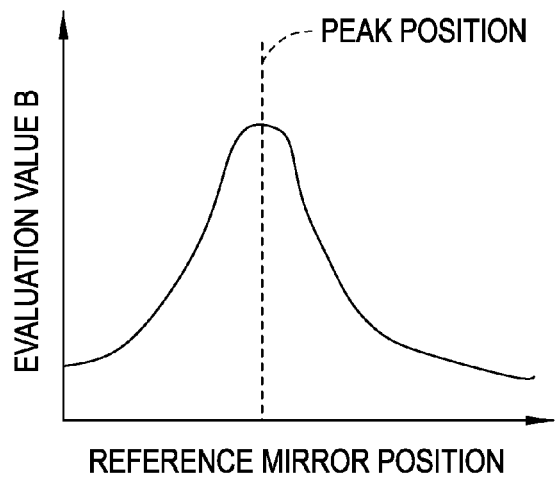
FIG. 10 illustrates an example of the result of calculation of an evaluation value B in accordance with the position of a reference mirror.

FIG. 10 is a diagram illustrating an example of the correspondence between the position of the reference mirror 31 and the calculation result for the evaluation value B. The horizontal axis shows the position of the reference mirror, and the vertical axis shows the evaluation value B corresponding to the position.

Here, the control unit 70 detects a peak for the evaluation value B based on the calculation result for the evaluation value B corresponding to the position of the reference mirror 31. Then, the control unit 70 stores in the memory 72 the position of the reference mirror 31 corresponding to the peak. The control unit 70 then causes the reference mirror 31 to be moved to the position corresponding to the peak of the evaluation value B. Generally, the position of the reference mirror 31 when a real image of the fundus appears in the tomographic image corresponds to the position at which the peak for the evaluation value B is detected. However, when the focus is wrong, the position of the reference mirror 31 when a virtual image appears in the tomographic image may correspond to the position at which the peak for the evaluation value B is detected.

According to the present embodiment, the first automatic optical path length adjustment and the focus adjustment are performed in parallel. Thus, when the focus adjustment is completed during the first automatic optical path length adjustment, the focused state of the tomographic image used for the first automatic optical path length adjustment is improved. Accordingly, the evaluation value B may be changed before and after the first automatic optical path length adjustment and, for this reason, the position at which the peak is detected may be changed. In this case, it is also sufficient if at least a part of the fundus tomographic image is displayed at a position on the monitor 75 for the first automatic optical path length adjustment. Therefore, during the first automatic optical path length adjustment, the peak position may not need to be properly detected. Namely, in the first automatic optical path length adjustment, the optical path length adjustment may be roughly performed. For this reason, the accuracy of peak detection need not be high.

As described above, the optical path length is roughly adjusted. Thus, at least a part of the fundus tomographic image is displayed at any position on the monitor 75.

The control unit 70 may stop the driving of the reference mirror 31 when the evaluation value B stops increasing and begins to decrease as the evaluation value B is acquired while the reference mirror 31 is moved in the predetermined steps. Also, the control unit 70 may estimate the position of the reference mirror 31 corresponding to the peak based on the result of calculation of the evaluation value B corresponding to the position of the reference mirror 31. This estimation is performed by generating an approximate curve showing the change in the evaluation value B, for example.

<Second Automatic Optical Path Length Adjustment (Fine Adjustment)>

Figure 11:
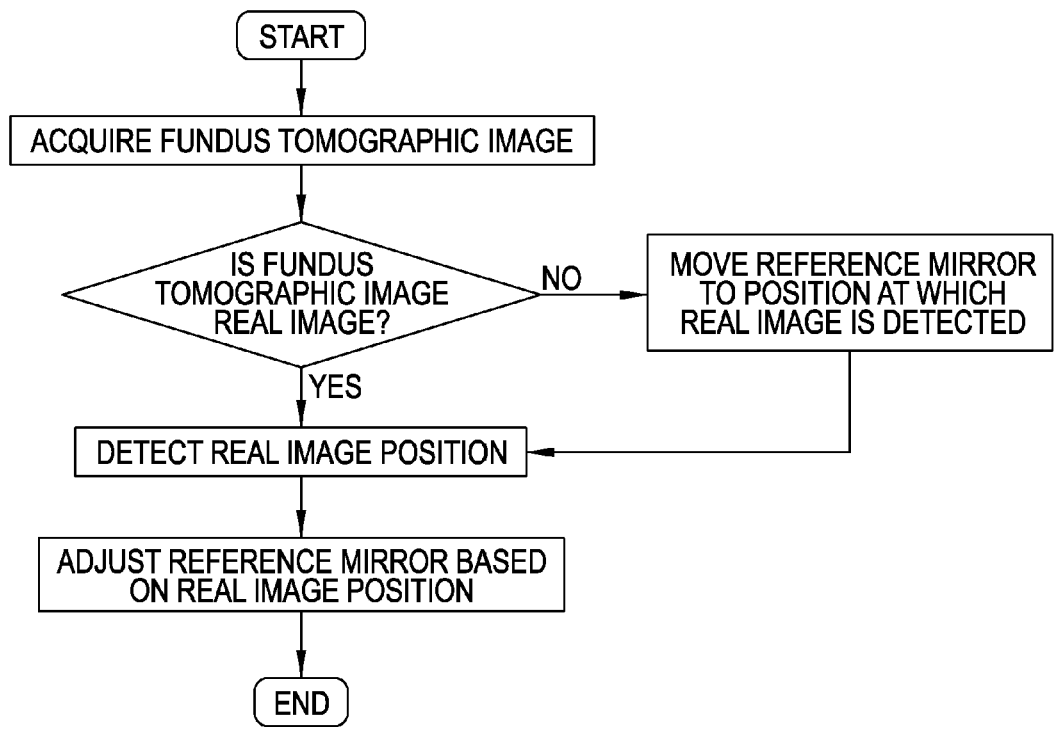
FIG. 11 is a flowchart illustrating the flow of a control operation for a second automatic optical path length adjustment.

FIG. 11 is a flowchart illustrating the flow of a control operation for the second automatic optical path length adjustment.

The control unit 70 starts the second automatic optical path length adjustment when the focusing lens 63 has been moved to the focus position. The control unit 70 readjusts, based on the output signal from the light receiving element 83, the position of the reference mirror 31 from the position adjusted by the first automatic optical path length adjustment.

Specifically, after the focus adjustment is completed, the control unit 70 performs the second automatic optical path length adjustment by moving the reference mirror 31 based on the tomographic image acquired by the focus adjustment.

Here, the control unit 70 determines whether the fundus tomographic image acquired from the first image range G1 after the focus adjustment is a real image or a virtual image. For example, the control unit 70 determines that the fundus tomographic image is a real image when the half-value width of the peak in the depth direction luminance distribution is smaller than a predetermined allowable width. On the other hand, the control unit 70 determines that the fundus tomographic image is a virtual image when the half-value width is greater than the predetermined allowable width. Whether the tomographic image is real or virtual may be determined by utilizing the difference in image quality between the real image and the virtual image. The determination may utilize tomographic image contrast, or the degree of rising of a tomographic image edge, in addition to the half-value width. Further, the determination may utilize the shape of the fundus tomographic image.

Upon determining that the acquired fundus tomographic image is a virtual image, the control unit 70 causes the reference mirror 31 to be moved in a direction where a real image is acquired (in a direction where the reference optical path becomes shorter). For example, the control unit 70 calculates an amount of movement of the reference mirror 31 such that the amount of displacement between the depth position S (optical path length coincidence position S) and the image detected position (predetermined fundus depth position) in the fundus becomes zero, and causes the reference mirror 31 to be moved by twice the calculated amount of movement. Thus, only the real image is acquired from the first image range G1. In this case, the amount of change of the depth position S corresponding to the amount of movement of the reference mirror 31 may be determined in advance. Accordingly, the control unit 70 can cause the reference mirror 31 to be moved such that the amount of displacement between the depth position S and the image detected position is equal to a predetermined amount. Thus, the control unit 70 can cause the fundus tomographic image to be displayed at a predetermined display position.

The technique for moving the reference mirror 31 is not limited thereto. For example, the control unit 70 may set, in advance, the amount of movement of the reference mirror 31 (predetermined offset amount) in the direction where the real image is acquired (the direction where the reference optical path becomes shorter) upon determining that the acquired fundus tomographic image is a virtual image. In this case, the control unit 70, upon determining that the fundus tomographic image is a virtual image, causes the reference mirror 31 to be moved by the predetermined offset amount.

Upon determining that the acquired fundus tomographic image is a real image, the control unit 70 determines the position of the real image. For example, the control unit 70 may regard the position at which the luminance distribution peak in the depth direction is detected as the image position. In this case, the control unit 70 calculates the amount of displacement between the pre-set optical path length adjustment position and the image position, and causes the reference mirror 31 to be moved so as to eliminate the amount of displacement (see JP 2010-12111 A).

The control unit 70 thus determines the fundus tomographic image obtained from the first image range G1 is real or virtual. In parallel, the control unit 70 may further determine whether or not a real image and a virtual image coexist in the first image range G1. For example, the control unit 70 determines an average position of the detected positions of the maximum luminance values for the respective scanning lines calculated as described above as an image position P1 for the fundus tomographic image. Then, the control unit 70 calculates the amount of displacement between the fundus depth position S (lower end position of the first image range G1) at which the optical path lengths of the measurement light and the reference light are coincident with each other and the image position (image detected position) P1. Namely, the control unit 70 calculates the image position of the fundus tomographic image with reference to the depth position S.

Then, when the image position P1 of the fundus tomographic image, which is calculated as described above, is in the vicinity of the lower end of the first image range G1 (such as in a ¼ region of the first image range G1 from the lower end thereof), the control unit 70 determines that a real image and a virtual image coexist in the first image range G1. In this case, the control unit 70 causes the reference mirror 31 to be moved by a predetermined amount in the direction where only the real image enters the first image range G1 (in the direction where the reference optical path becomes shorter). In this case, the direction of movement and the amount of movement of the reference mirror 31 for achieving the state in which only the real image exists in the first image range G1 from the state in which the real image and the virtual image coexist in the range may be determined by experiment or simulation in advance and then stored in the memory 72.

<Timing of First Automatic Optical Path Length Adjustment and Focus Adjustment>

When the control for the second automatic optical path length adjustment is started, the timing of completion of the first automatic optical path length adjustment may differ from the timing of completion of the focus adjustment. For example, there are the cases where the first automatic optical path length adjustment is completed earlier than the focus adjustment, the first automatic optical path length adjustment is completed later than the focus adjustment, and the first automatic optical path length adjustment and the focus adjustment are substantially simultaneously completed.

In the case where the first automatic optical path length adjustment is completed earlier than the focus adjustment, the tomographic image may cease to be displayed because of the eye movement during the focus adjustment, or the like. If the second automatic optical path length adjustment is started in this state, the second automatic optical path length adjustment may result in a failure.

In the case where the first automatic optical path length adjustment is completed later than the focus adjustment, the second automatic optical path length adjustment may be started after completion of the focus adjustment and before completion of the first automatic optical path length adjustment. In this case, the second automatic optical path length adjustment is started before at least a part of the fundus tomographic image is displayed somewhere on the monitor 75. Thus, the second automatic optical path length adjustment may result in a failure.

Accordingly, the control unit 70 detects the timing of completion of the first automatic optical path length adjustment and the timing of completion of the focus adjustment. The control unit 70 performs control as described below, except for the case where the first automatic optical path length adjustment and the focus adjustment are substantially simultaneously completed.

Figure 12:
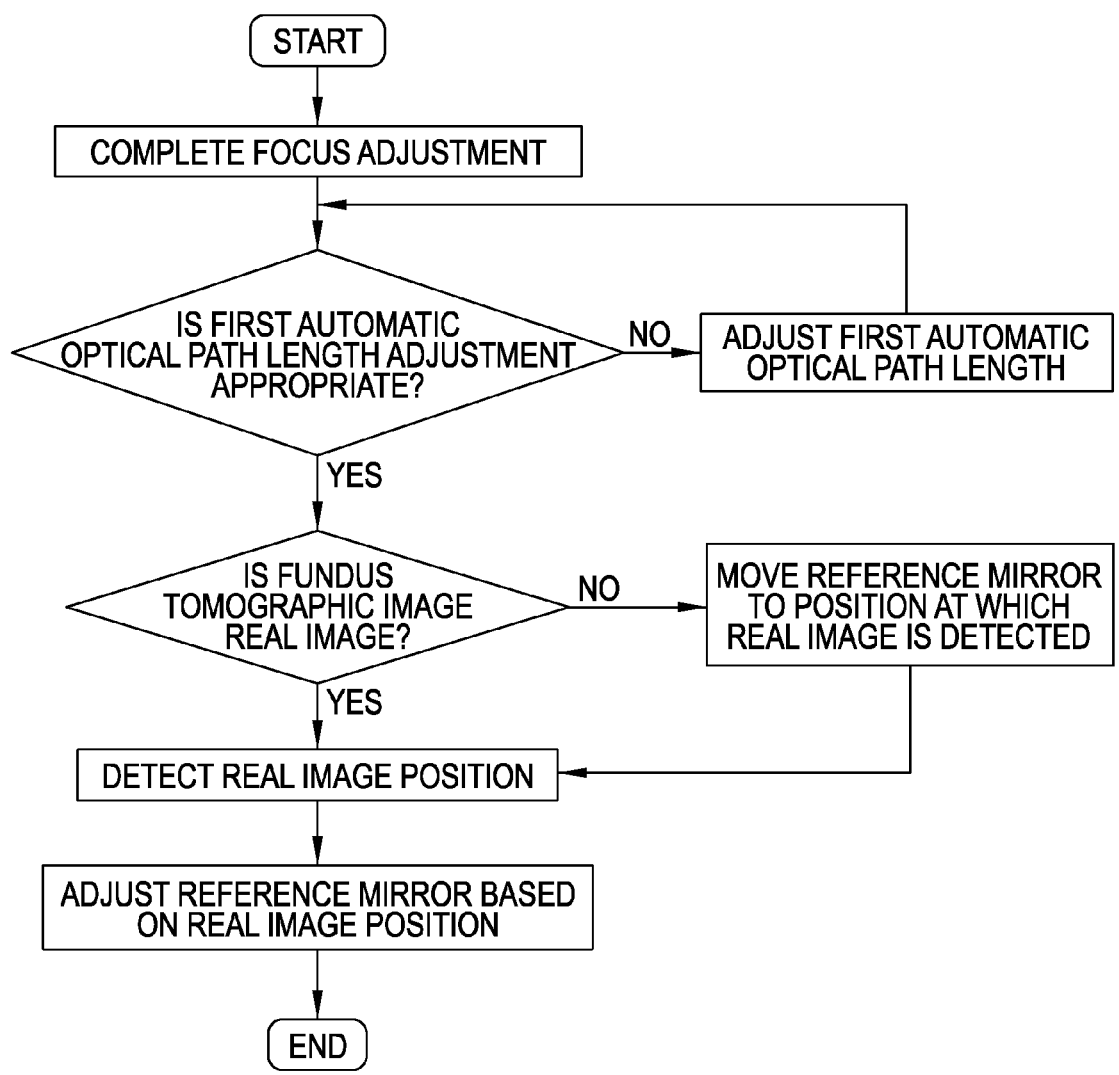
FIG. 12 is a flowchart illustrating the flow of a control operation for the second automatic optical path length adjustment when the first automatic optical path length adjustment and the focus adjustment have not been completed substantially simultaneously.

FIG. 12 is a flowchart illustrating the flow of a control operation for the second automatic optical path length adjustment in the case where the first automatic optical path length adjustment and the focus adjustment are not substantially simultaneously completed.

When the focus adjustment is completed, the control unit 70 determines the propriety of the first automatic optical path length adjustment. For example, the control unit 70 sets a predetermined threshold value in advance. The control unit 70 determines whether or not the detected value (such as the evaluation value B or the luminance value) has exceeded the threshold value, and judges the propriety of the first automatic optical path length adjustment based on the result of determination.

When judging that the first automatic optical path length adjustment is successful (properly completed), the control unit 70 determines whether the fundus tomographic image acquired after the focus adjustment is a real image or a virtual image. When determining that the acquired fundus tomographic image is a virtual image, the control unit 70 causes the reference mirror 31 to be moved in the direction where a real image is acquired (in the direction where the reference light becomes shorter). When determining that the acquired fundus tomographic image is a real image, the control unit 70 determines the position of the real image. For example, the control unit 70 regards the position at which the luminance distribution peak in the depth direction is detected as the image position. The control unit 70 calculates the amount of displacement between the pre-set optical path length adjustment position and the image position. The control unit 70 then causes the reference mirror 31 to be moved so as to eliminate the amount of displacement.

When determining that the first automatic optical path length adjustment has failed, the control unit 70 performs the first automatic optical path length adjustment again. The control unit 70 may stop the optimization (optimization control) every time the first automatic optical path length adjustment fails. Alternatively, the control unit 70 may stop the optimization when the first automatic optical path length adjustment has failed several times. When repeating the first automatic optical path length adjustment, the control unit 70 may move the initial position of the reference mirror 31 (optical member for optical path length adjustment) to the movement limit position K1 or the movement limit position K2. Alternatively, the control unit 70 may set the initial position of the reference mirror 31 based on the evaluation value B obtained by the previous first automatic optical path length adjustment. Further, the control unit 70 may perform the direction of movement of the reference mirror 31 from the initial position based on the evaluation value B obtained by the previous first automatic optical path length adjustment.

The control unit 70 may search for the fundus tomographic image from the position of the reference mirror 31 (optical member for optical path length adjustment) at the time of completion of the first automatic optical path length adjustment. Thus, the time for moving the reference mirror 31 to the movement limit position K1 or the movement limit position K2 can be shortened. For example, the control unit 70 determines whether the position of the reference mirror 31 at the time of completion of the first automatic optical path length adjustment is closer to the movement limit position K1 or the movement limit position K2. Then, the control unit 70 causes the reference mirror 31 to be moved to the limit position determined to be closer. The control unit 70 searches for the position at which the fundus tomographic image is acquired based on the tomographic image corresponding to the position. In the absence of the fundus tomographic image, the control unit 70 searches for the position at which the fundus tomographic image is acquired while causing the reference mirror 31 to be moved toward the other movement limit position.

When the optimization has failed, the control unit 70 may cause the monitor 75 to display a failure indication so as to allow the examiner to select whether or not the optimization is to be repeated.

The control unit 70, upon determining that the first automatic optical path length adjustment that has been repeated is a success, determines whether the acquired fundus tomographic image is a real image or a virtual image. The control unit 70 then performs control in the same way as described above in accordance with the result of determination.

When determining that the adjustment has failed based on the judgment of the propriety of the first automatic optical path length adjustment, the control unit 70 may perform the focus adjustment again together with the first automatic optical path length adjustment.

Regarding the determination as to whether the fundus tomographic image that has been acquired after the focus adjustment is a real image or a virtual image and the determination as to the presence or absence of the fundus tomographic image, one of the determinations may be performed first before the other. Alternatively, both of them may be performed simultaneously. Of course, the control unit 70 may perform readjustment based on the result of one or the other determination.

As described above, optimization is performed such that the first automatic optical path length adjustment and the focus adjustment are performed in parallel and then the second automatic optical path length adjustment is performed. In this case, the control unit 70 performs the first automatic optical path length adjustment by using the OCT optical system 200 while performing the focus adjustment by using the SLO optical system 300. Thus, the control unit 70 can perform the focus adjustment and the first automatic optical path length adjustment in parallel.

Generally, in the optical path length adjustment prior to the focus adjustment, the luminance detected from the image is weak. Thus, it is difficult to determine whether the fundus tomographic image is a real image or a virtual image. However, in the present apparatus, the position at which the fundus tomographic image is acquired can be detected based on the fundus tomographic image even when the focus is not adjusted. Namely, while it is difficult to perform the second optical path length adjustment when the focus adjustment is not yet completed, it is possible to perform the first optical path length adjustment. Accordingly, in the present apparatus, it is not necessary to withhold the start of the first optical path length automatic adjustment until the focus adjustment is completed. Thus, in the present apparatus, optimization can be performed smoothly in a short time. Namely, the present apparatus can adjust the photographing conditions in a preferred manner.

<Polarizer Adjustment>

The control unit 70 adjusts the polarization state by driving the polarizer 33 based on the light receiving signal output from the light receiving element 83 after the second automatic optical path length adjustment.

Specifically, the control unit 70 causes the polarizer 33 to be moved from the initial position to a movement start position. The initial position of the polarizer 33 is an intermediate position between the first movement limit position and the second movement limit position. The movement start position of the polarizer 33 for polarizer adjustment is the first movement limit position or the second movement limit position.

The control unit 70 selects the movement start position of the polarizer 33 from the first movement limit position or the second movement limit position. Then, the control unit 70 causes the polarizer 33 to be moved from the intermediate position (initial position) to the selected movement start position. For example, the control unit 70 selects the first movement limit position as the movement start position, and causes the polarizer 33 to be moved toward such a position. Then, the control unit 70 causes the polarizer 33 to be moved from the first movement limit position toward the second movement limit position direction. When the movement start position is the second movement limit position, the control unit 70 causes the polarizer 33 to be moved toward the first movement limit position direction in predetermined steps. The control unit 70 then successively acquires the images on the screen of the monitor 75 corresponding to the moving positions, and searches for the position at which the interference light can be strongly received (position at which the polarization states of the measurement light and the reference light are aligned).

During the search for the position with the aligned polarization states, the control unit 70 analyzes the image acquired at the current position and calculates the evaluation value B each time the polarizer 33 is stopped at the discretely set moving positions.

The control unit 70 causes the polarizer 33 to be moved to the movement limit position different from the movement start position in 5° steps. The movement steps are not limited to the above and may be 10° or 20°, for example. The steps may be arbitrarily set.

Here, the control unit 70 detects the peak value for the evaluation value B from the result of calculation of the evaluation value B corresponding to the position of the polarizer 33. Then, the control unit 70 causes the polarizer 33 to be moved to the position corresponding to the peak value. In this way, the polarizer adjustment is completed.

As described above, optimization control is completed, whereby the fundus site of interest to the examiner can be observed with high sensitivity and high resolution.

<Modification>

According to the present embodiment, the observation optical system for acquiring the front image of the fundus of the examinee's eye is the SLO optical system 300. On the basis of the front image acquired by the SLO optical system 300, the focus position of the OCT optical system 200 is adjusted. However, this is merely an example. The observation optical system may be a member that includes a light source for irradiating the examinee's eye with infrared light and a light receiving element for receiving reflected light from the examinee's eye, and that obtains the front image of the examinee's eye based on a light receiving signal from the light receiving element. An example of such a member is a fundus camera. In this case, focus position information about the fundus camera optical system is acquired based on an infrared fundus image obtained by the fundus camera. In this regard, the focus position detection technique based on the SLO fundus image as described above can be applied.

The method for acquiring the focus position information is not limited to the above technique. The focus position information may be acquired by a method for acquiring the focus position information based on a light receiving signal output from a light receiving element that receives the light reflected from the fundus. For example, the focus position information may be acquired by the following method. Namely, first, a projecting optical system is used to project a focusing target (such as a split target) on the fundus of the examinee's eye. A target image produced by the light reflected from the fundus (fundus reflected image) is received by the light receiving element. The focus position information is then acquired based on the light receiving signal output from the light receiving element.

According to the present embodiment, the focus adjustment may be performed by using the light reflected from the fundus from the OCT optical system 200. In this method, for example, a detector extracts part of a signal corresponding to the light reflected from the fundus from the OCT optical system 200. On the basis of the intensity of the signal detected from the detector, the focus adjustment is performed. For example, the focus adjustment is performed such that the signal intensity detected from the detector shows a peak.

According to the present embodiment, the first automatic optical path length adjustment is performed based on the evaluation value B. However, this is merely an example. During the first automatic optical path length adjustment, the control unit 70 may determine whether the tomographic image is a real image or a virtual image (real/virtual determination), as in the second automatic optical path length adjustment. The control unit 70 may then perform the optical path length adjustment based on the result of the determination. In the present apparatus, because the first automatic optical path length adjustment and the focus adjustment are performed in parallel, the control unit 70 can perform the real/virtual determination. During the first automatic optical path length adjustment, the focus adjustment is not completed. Thus, it is difficult to perform fine-adjustment of the optical path length. Accordingly, the control unit 70 fine-adjusts the optical path length by the second automatic optical path length adjustment after the focus adjustment. Namely, the control unit 70 detects the image position of the fundus tomographic image in the second automatic optical path length adjustment. The control unit 70 then causes the reference mirror 31 to be moved by a predetermined amount in the direction where a real image is acquired.

During the second automatic optical path length adjustment, the control unit 70 performs the optical path length adjustment based on the result of the real/virtual determination. However, this is merely an example, and the control unit 70 may adjust the optical path length based on the evaluation value B during the second automatic optical path length adjustment as during the first automatic optical path length adjustment. In this case, during the first automatic optical path length adjustment, the predetermined steps for moving the reference mirror may be made longer (such as 5 mm), while, during the second automatic optical path length adjustment, the predetermined steps for moving the reference mirror may be made shorter (such as 2 mm). In this way, the time required for the first automatic optical path length adjustment is shortened. Further, the second automatic optical path length adjustment can be performed accurately. Of course, the present apparatus may be configured such that the intervals of the predetermined steps can be arbitrarily changed.

According to the present embodiment, the control unit 70 performs the focus adjustment by using the SLO optical system 300. However, this is merely an example, and the control unit 70 may cause the focusing lens 24 of the OCT optical system 200 to be moved based on the focus position information about the SLO optical system 300 that is obtained by the first focus adjustment. Then, the control unit 70 may acquire the focus position information about the OCT optical system 200 based on the tomographic image acquired by the OCT optical system 200. The control unit 70 may cause the focusing lens 24 to be moved to the focus position based on the focus position information. Thus, the accuracy of focus adjustment can be further increased.

In the above optimization, the next adjustment is performed after completion of the preceding adjustment with the exception of part of the optimization control (determination of the propriety of the first optical path length adjustment). However, this is merely an example. In another example, the control unit 70 may determine whether optimization has been successful based on the luminance information of the tomographic image, and may stop optimization depending on the result of determination. The control unit 70, upon determining that optimization has failed, repeats optimization. The control unit 70 may stop optimization every time optimization fails. The control unit 70 may stop optimization when optimization has failed several times. Further, upon optimization failure, an optimization failure indication may be displayed on the monitor 75, for example, so that the examiner can be allowed to select whether to perform re-optimization.

When the control unit 70 determines that a failure occurred at a step during optimization (such as focus adjustment), the control unit 70 may adjust a member not related to the step before repeating optimization. For example, the control unit 70, when the focus adjustment has failed, may cause the polarizer 33 to be rotated by a predetermined angle (such as 90°) so as to change the polarization state. Thereby, the light-receiving state of the fundus tomographic image can be changed, so that the optimization may be made possible when repeated.

In the foregoing description, the optimization includes the optical path length adjustment, the focus adjustment, and the polarizer adjustment. However, the adjustments included in the optimization are not limited to the above. For example, the optimization may not include the polarizer adjustment. In this case, the time required for optimization can be shortened, although the sensitivity and resolution of the fundus tomographic image may be lowered.

In the foregoing description, the optimization is performed in the order of the first automatic optical path length adjustment, the focus adjustment, the second automatic optical path length adjustment, and the polarizer adjustment. However, this is merely an example. In another example, the polarizer adjustment may be performed between completion of the first automatic optical path length adjustment and the focus adjustment and the implementation of the second automatic optical path length adjustment.

According to the present embodiment, the focus adjustment may be performed twice before and after the second optical path length adjustment. In this case, the control unit 70 may perform the first focus adjustment coarsely such that the optical path length can be finely adjusted by the second optical path length adjustment. The control unit 70 may achieve focusing by the second focus adjustment after completion of the fine adjustment of the optical path length by the second optical path length adjustment.

According to the present embodiment, the second automatic optical path length adjustment is started after completion of the focus adjustment. However, this is merely an example, and the second automatic optical path length adjustment may be performed after completion of the focus adjustment and the first automatic optical path length adjustment.

In the foregoing description, the control unit 70 makes the real image/virtual image determination for the fundus tomographic image by utilizing the luminance distribution in the tomographic image. However, this is merely an example. The control unit 70 may compare the cross-sectional shape of the tomographic image provided when a real image of the fundus tomographic image is acquired with the cross-sectional shape of the tomographic image provided when a virtual image of the fundus tomographic image is acquired so as to make the real image/virtual image determination in consideration of the result of comparison (Namely, the control unit 70 may set conditions that enable such determination). For example, the control unit 70 utilizes the fact that the real image and the virtual image are mutually symmetrical to each other with respect to a predetermined depth position (such as the depth position S in FIG. 2). More specifically, the control unit 70 extracts a retinal pigment epithelium portion from the first image range G1 of the fundus tomographic image by image processing. The image processing involves, for example, extraction of data relating to luminance value exceeding a predetermined threshold value that corresponds to the luminance value of the retinal pigment epithelium. Then, the control unit 70, based on the curved shape of the extracted retinal pigment epithelium portion, may make the real image/virtual image determination for the fundus tomographic image. This technique may be applicable to a configuration in which dispersion correction is performed by using an optical member. Of course, this technique may be applicable to a configuration in which optical dispersion correction and software-based dispersion correction are used in combination.

In the foregoing description, the photographing conditions are adjusted based on the depth profile after Fourier transform. However, this is merely an example, and the photographing conditions may be adjusted based on the light receiving signal output from a detector. For this adjustment, the spectral data before Fourier transform may be used.

In the foregoing description, the present apparatus includes the spectral domain OCT (OCT optical system 200) using a spectrometer. However, this is merely an example, and the present apparatus may be provided with a SS-OCT (swept source OCT) including a wavelength variable light source.

The optical fiber 38c may be rotated by the driving mechanism 34 so as to change the polarization direction of the reference light. Namely, the optical fiber 38c and the driving mechanism 34 may be used as the polarizer 33 for polarization direction adjustment.

The fundus photographing apparatus according to the present disclosure may include the following first to tenth fundus photographing apparatuses. A first fundus photographing apparatus is a fundus photographing apparatus that obtains a tomographic image of the fundus of an examinee's eye, the fundus photographing apparatus including: an interference optical system configured to split a light flux output from a light source into measurement light and reference light, that guides the measurement light flux to the fundus of the examinee's eye, that guides the reference light to a reference optical system, and that then detects an interference state of the measurement light reflected from the fundus of the examinee's eye and the reference light by a detector; an optical scanner disposed in the optical path of the measurement light to scan the fundus of the examinee's eye with the measurement light; a focus detection unit that includes a light receiving element for receiving light including reflected light from the fundus of the examinee's eye and configured to detect a focus position with respect to the fundus of the examinee's eye based on an output signal from the light receiving element; a first drive unit that drives a first optical member disposed in the optical path of the measurement light to correct the diopter scale with respect to the examinee fundus; a focus adjustment unit that moves the first optical member to the focus position detected by the focus detection unit; a second drive unit that drives a second optical member disposed in the optical path of the measurement light or the reference light to adjust an optical path length difference between the measurement light and the reference light; and an optical path length adjustment unit that causes, in parallel with the operation of the focus detection unit, the second optical member to be moved to a position at which the examinee's eye tomographic image is acquired based on the output signal output from the detector, and that readjusts the position of the second optical member based on the output signal output from the detector after the first optical member is moved to the focus position by the focus adjustment unit.

A second fundus photographing apparatus is based on the first fundus photographing apparatus, in which the focus detection unit includes: an irradiation optical system that irradiates the fundus of the examinee's eye with illuminating light; a light receiving optical system that receives the light reflected from the fundus with the light receiving element; and a third drive unit that drives a third optical member disposed in the light receiving optical system. The focus detection unit also provides the function of a fundus observation optical system for obtaining a front fundus image of the fundus of the examinee's eye based on the output signal from the light receiving element, controls the driving of the third drive unit to move the third optical member, and detects the focus position with respect to the fundus of the examinee's eye based on the front fundus image acquired at each position of the third optical member.

A third fundus photographing apparatus is based on the first or second fundus photographing apparatus, in which the interference optical system is an interference optical system configured to split the light flux output from the light source into the measurement light and the reference light, that guides the measurement light flux to the fundus of the examinee's eye, that guides the reference light to the reference optical system, and that then detects spectral information about light combining the measurement light reflected from the fundus of the examinee's eye and the reference light by the detector, wherein the tomographic image of the fundus of the examinee's eye is obtained through Fourier analysis of the spectral information detected by the detector.

A fourth fundus photographing apparatus is based on the third fundus photographing apparatus, in which the optical path length adjustment unit determines, after the first optical member is moved to the focus position by the focus adjustment unit, whether the fundus tomographic image acquired in a predetermined image region is a real image or a virtual image, and readjusts the position of the optical member in accordance with the result of determination.

A fifth fundus photographing apparatus is based on any one of the first to fourth fundus photographing apparatuses, in which the optical path length adjustment unit controls the driving of the second drive unit to move the second optical member, and causes the second optical member to be moved, based on the output signal output from the detector at each position of the second optical member, to a position at which the examinee's eye tomographic image is acquired.

A sixth fundus photographing apparatus is based on any one of the first to fifth fundus photographing apparatuses, in which the optical path length adjustment unit roughly adjusts the optical path length based on the signal intensity of the output signal output from the detector so as to include the fundus tomographic image in the tomographic image, while the optical path length adjustment unit acquires position information about the fundus tomographic image in a depth direction based on the output signal output from the detector, and severely adjusts the optical path length based on the acquired position information so as to acquire the fundus tomographic image at a predetermined depth position.

A seventh fundus photographing apparatus is based on the first to sixth fundus photographing apparatuses, including a polarization adjustment unit that substantially aligns polarization states of the measurement light and the reference light by driving a polarization element disposed in the optical path of the measurement light or the optical path of the reference light. The polarization adjustment unit adjusts the polarization states by driving the polarization element based on the output signal output from the detector after the position of the optical member is readjusted.

An eighth fundus photographing apparatus is based on the first to seventh fundus photographing apparatuses, including an adjustment determination unit that determines whether optimization adjustment is successful based on luminance information of the tomographic image, and an optimization control unit that stops optimization adjustment based on the result of determination by the adjustment determination unit.

A ninth fundus photographing apparatus is based on the first to eighth fundus photographing apparatuses, in which the optical path length adjustment unit, simultaneously with the operation of the focus detection unit, moves the second optical member to the position at which the examinee's eye tomographic image is acquired based on the output signal output from the detector.

A tenth fundus photographing apparatus is based on the first to ninth fundus photographing apparatus, in which the optical path length adjustment unit determines, after the first optical member is moved to the focus position by the focus adjustment unit, the presence or absence of the fundus tomographic image in the tomographic image, and, when it is determined that the fundus tomographic image is absent, moves the second optical member again by controlling the driving of the second drive unit, wherein the second optical member is moved to the position at which the examinee's eye tomographic image is acquired based on the output signal output from the detector at each position of the second optical member.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus photographing apparatus for obtaining a tomographic image of a fundus of an examinee's eye, comprising:
   an interference optical system configured to split a light flux output from a light source into measurement light and reference light, and detect an interference state of the measurement light reflected by the fundus of the examinee's eye and the reference light by a detector;
   an optical scanner disposed in an optical path of the measurement light to scan the fundus of the examinee's eye with the measurement light;
   a focus detection unit having a light receiving element for receiving light including reflected light from the fundus of the examinee's eye, and configured to detect a focus position with respect to the fundus of the examinee's eye based on an output signal from the light receiving element;
   a first optical member disposed in the optical path of the measurement light;
   a focus adjustment unit that corrects a diopter scale with respect to the examinee fundus by moving the first optical member to the focus position detected by the focus detection unit;
   a second optical member disposed in the optical path of the measurement light or the reference light;
   an optical path length adjustment unit that adjusts an optical path length difference between the measurement light and the reference light; and
   a control unit that is configured to simultaneously control the focus adjustment unit and the optical path length adjustment unit such that the second optical member is moved to a position at which a tomographic image of the fundus of the examinee's eye is acquired based on an output signal from the detector and in parallel the first optical member is moved to the focus position detected by the focus detection unit, and the control unit is further configured to readjust the position of the second optical member based on the output signal from the detector after the first optical member is moved to the focus position detected by the focus detection unit.

2. The fundus photographing apparatus according to claim 1, wherein the focus detection unit
   includes an irradiation optical system that irradiates the fundus of the examinee's eye with illuminating light, and a light receiving optical system that includes a third optical member and that receives the reflected light from the fundus by the light receiving element, and
   acquires a front fundus image of the fundus of the examinee's eye based on the output signal from the light receiving element while moving the third optical member, and detects the focus position with respect to the fundus of the examinee's eye based on the front fundus image in accordance with the position of the third optical member.

3. The fundus photographing apparatus according to claim 1, wherein the interference optical system is configured to
   split the light flux output from the light source into the measurement light and the reference light,
   guide the measurement light flux to the fundus of the examinee's eye while guiding the reference light to a reference optical system,
   detect spectral information about synthetic light of the measurement light reflected by the fundus of the examinee's eye and the reference light by the detector, and
   obtain a tomographic image of the fundus of the examinee's eye through Fourier analysis of the spectral information.

4. The fundus photographing apparatus according to claim 3, wherein the optical path length adjustment unit is configured to
   determine, after the first optical member is moved to the focus position by the focus adjustment unit, whether the fundus tomographic image acquired in a predetermined image region is a real image or a virtual image, and
   readjust the position of the second optical member in accordance with the result of the determination.

5. The fundus photographing apparatus according to claim 1, wherein the optical path length adjustment unit is configured to move, based on the output signal from the detector in accordance with the position of the second optical member, the second optical member to the position at which the tomographic image of the fundus of the examinee's eye is acquired.

6. The fundus photographing apparatus according to claim 1, wherein the optical path length adjustment unit is configured to
   adjust the optical path length difference based on the intensity of the output signal from the detector so as to include the fundus tomographic image in the tomographic image, and
   acquire position information about the fundus tomographic image in a depth direction based on the output signal from the detector, and adjusts the optical path length difference based on the acquired position information so as to acquire the fundus tomographic image at a predetermined depth position.

7. The fundus photographing apparatus according to claim 1, further comprising:
   a polarization element disposed in the optical path of the measurement light or the optical path of the reference light; and
   a polarization adjustment unit that causes polarization states of the measurement light and the reference light to be substantially aligned by adjusting the polarization state of the reference light by driving the polarization element based on the output signal from the detector after the position of the second optical member is readjusted.

8. The fundus photographing apparatus according to claim 1, further comprising:
   an adjustment determination unit that determines whether, based on the luminance information of the tomographic image, the adjustments by the focus adjustment unit and the optical path length adjustment unit are successful; and an adjustment termination unit that terminates subsequent adjustments when the adjustment determination unit determines that one or the other adjustment fails.

9. The fundus photographing apparatus according to claim 1, wherein the control unit is configured to control the focus adjustment unit and the optical path length adjustment unit such that the optical path length adjustment unit moves the second optical member to the position at which the tomographic image of the fundus of the examinee's eye is acquired based on the output signal from the detector simultaneously with the start of detection of the focus position detected by the focus detection unit.

10. The fundus photographing apparatus according to claim 1, wherein the optical path length adjustment unit is configured to determine the presence or absence of the fundus tomographic image in the tomographic image after the first optical member is moved to the focus position by the focus adjustment unit, and move, upon determining that the fundus tomographic image is absent, the second optical member to the position at which the tomographic image of the fundus of the examinee's eye is acquired based on the output signal from the detector in accordance with the position of the second optical member.

\* \* \* \* \*